US007527429B2

(12) United States Patent
Francke

(10) Patent No.: US 7,527,429 B2
(45) Date of Patent: May 5, 2009

(54) IMAGING ARRANGEMENT AND METHOD

(75) Inventor: Tom Francke, Sollentuna (SE)

(73) Assignee: XCounter AB, Danderyd (SE)

( * ) Notice: Subject to any disclaimer, the term of this patent is extended or adjusted under 35 U.S.C. 154(b) by 161 days.

(21) Appl. No.: 11/652,581

(22) Filed: Jan. 12, 2007

(65) Prior Publication Data

US 2007/0223650 A1 Sep. 27, 2007

(30) Foreign Application Priority Data

Mar. 21, 2006 (SE) .................................... 0600636
Nov. 27, 2006 (SE) .................................... 0602518

(51) Int. Cl.
*H05G 1/02* (2006.01)

(52) U.S. Cl. ........................................ 378/197; 378/21

(58) Field of Classification Search .................. 378/22, 378/62, 21, 196, 197
See application file for complete search history.

(56) References Cited

U.S. PATENT DOCUMENTS 4,204,124 A * 5/1980 Kowalski ....................... 378/9
4,303,830 A * 12/1981 Heinzelmann et al. ......... 378/9
4,349,740 A 9/1982 Grassmann et al.
6,337,482 B1 1/2002 Francke
6,353,653 B1 * 3/2002 Edic .............................. 378/8
6,476,397 B1 11/2002 Francke
6,477,223 B1 11/2002 Francke
6,522,722 B1 2/2003 Francke
6,627,897 B1 9/2003 Francke
6,784,436 B2 8/2004 Francke
6,794,656 B2 9/2004 Francke
6,818,901 B2 11/2004 Francke
6,856,669 B2 2/2005 Francke
6,873,682 B2 3/2005 Francke
6,940,942 B2 9/2005 Ullberg
6,970,533 B2 11/2005 Francke
7,006,597 B2 2/2006 Francke (Continued)

FOREIGN PATENT DOCUMENTS

DE 39 31 531 4/1990

(Continued)

OTHER PUBLICATIONS

International-Type Search Report dated Sep. 5, 2007 for corresponding Swedish application.

*Primary Examiner*—Chih-Cheng G Kao
(74) *Attorney, Agent, or Firm*—Harness, Dickey & Pierce, P.L.C.

(57) ABSTRACT

The invention relates to an imaging arrangement 1 for obtaining imaging data of an object 7. The imaging arrangement 1 comprises a support structure 3 having an axis of rotation 9 and comprising means 10 for rotating the support structure 3; a pair of first and second radiation modules 2*a*, 2*b* fixedly arranged on the support structure 3 along a radius perpendicular to the axis of rotation 9, wherein each of the radiation modules 2*a*, 2*b* comprises a radiation source 6*a*, 6*b* simultaneously emitting radiation; a radiation detector 4 for detecting radiation as emitted from the radiation modules 2*a*, 2*b* and passed through the object 7 being imaged; and a collimator 14 arranged between, as seen in a direction parallel to the axis of rotation 9, the pair of radiation modules 2*a*, 2*b* and the radiation detector 4. The invention also relates to a corresponding method.

14 Claims, 3 Drawing Sheets

1 9 3 3a 6a 6b 2a 2b 8a 8b 10 14 4 5 7

U.S. PATENT DOCUMENTS

| | | | | |
|---|---|---|---|---|
| 7,016,458 | B2 | 3/2006 | Francke | |
| 7,085,343 | B2 * | 8/2006 | Shinno et al. | 378/9 |
| 2005/0067570 | A1 | 3/2005 | Retterath et al. | |
| 2005/0117694 | A1 * | 6/2005 | Francke | 378/4 |
| 2005/0226367 | A1 * | 10/2005 | Francke | 378/22 |

FOREIGN PATENT DOCUMENTS

| | | |
|---|---|---|
| WO | WO 2005/094688 A1 | 10/2005 |
| WO | WO 2005/119297 | 12/2005 |

* cited by examiner

IMAGING ARRANGEMENT AND METHOD

PRIORITY STATEMENT

This application claims benefit of priority under 35 U.S.C. §119 from Swedish Patent Publication No. SE 0600636-5, filed on Mar. 21, 2006, and Patent Application No. SE 0602518-3, filed on Nov. 27, 2006, in the Swedish Patent Office, the disclosures of which are incorporated herein by reference in their entirety.

FIELD OF THE INVENTION

The present invention relates generally to apparatuses and methods for obtaining time resolved imaging data of an object.

BACKGROUND OF THE INVENTION

Medical X-ray imaging of patients, for example angiography, is most important and a frequently used examination method. Angiography is a radiological method for examination of blood or lymph vessels. Blood has the same radiodensity as the surrounding tissues and a radiocontrast agent (which absorbs X-rays) is therefore added to the blood to make angiography visualization possible. A catheter is inserted into the vessel, e.g. by Seldinger technique, and a water soluble contrast agent is injected into the vessel, after which a series of X-ray images of the vessel is taken. Examinations of arteries, veins and lymph vessels are denoted arteriography, flebography and lymphography, respectively. Arteriography is a commonly applied examination method and includes angiocardiography for examination of the heart, coronary angiography for examination of the coronary arteries of the heart and aortography for examination of the aorta.

The X-ray images may be taken as either still images displayed on a fluoroscope, or may be taken as motion images. Fluoroscopy requires high concentrations of contrast agents, for example iodinated contrast agents. Fluoroscopy involves the use of ionizing radiation and all fluoroscopic procedures therefore pose a potential health risk to the patient. Radiation doses that the patient is exposed to depend greatly on the size of the patient as well as length of the procedure and exposure times vary depending on the procedure being performed.

The International patent publication WO 2005/094688, assigned to the same applicant as the present application and the contents of which is hereby incorporated by reference, describes an arrangement for obtaining imaging data. Although the invention described in this document provides improvements within the field of imaging, there is still a need for further improvements in obtaining images of an object at high repetition rate.

The examination of blood or lymph vessels in angiography is a time-dependent process, which puts requirements on the repetition rate of the detector used. When performing angiography it is therefore important to rapidly obtain the images. Further, in angiocardiography it is important to take the motion of the heart into consideration.

In view of the above, it would be desirable to provide improvements within the field of medical imaging and in particular angiography.

SUMMARY OF THE INVENTION

It is an object of the invention to provide improvements in medical imaging techniques, such as angiography, and in particular to provide increased contrast resolution of images obtained by angiography.

It is another object of the invention to provide an imaging arrangement for angiography that can produce high-quality three-dimensional images with high image contrast, while exposing the object that is being examined for as low radiation dose as possible.

It is yet another object of the invention to provide an imaging arrangement for angiography wherein the amount of iodinated contrast agent administered into a patient can be minimized.

It is still another object of the invention to provide an imaging arrangement for angiography having a high repetition rate.

These objects, among others, are achieved by an imaging arrangement and method as claimed in the appended claims.

In accordance with the invention, an imaging arrangement for obtaining imaging data of an object is provided. The imaging arrangement comprises a support structure having an axis of rotation and comprising means for rotating the support structure; a pair of first and second radiation modules fixedly arranged on the support structure along a radius perpendicular to the axis of rotation, wherein each of the radiation modules comprises a radiation source simultaneously emitting radiation; a radiation detector for detecting radiation as emitted from the radiation modules and passed through the object being imaged, wherein the radiation detector comprises a number of direction sensitive line detectors, each being directed towards either one of the two radiation sources in order to allow a ray bundle of radiation to enter the line detector; and a collimator arranged between, as seen in a direction parallel to the axis of rotation, the pair of radiation modules and the radiation detector. The invention provides an improved contrast resolution, whereby the amount of iodinated contrast agent can be minimized and health hazards for the patient can be reduced substantially.

In accordance with an embodiment of the invention, each of the direction sensitive line detectors is adapted to record a plurality of line images of radiation as transmitted through the object from the pair of radiation modules. Further, every second line detector may be arranged to record radiation from the first radiation module and every second line detector may be arranged to record radiation from the second radiation module. Simultaneous recording of data from the two radiation sources is enabled resulting in an increased three-dimensional resolution, shorter acquisition time and increased contrast resolution.

In another embodiment of the invention, two or more pairs of first and second radiation modules is provided, wherein each pair has an associated collimator and radiation detector. The radiation detector of each pair is then arranged to consecutively image the object during a revolution of the imaging arrangement. The imaging arrangement may then be rotated at a lower speed or several different phases of the heartbeat may be recorded in a single rotation of the imaging arrangement.

In yet another embodiment of the invention, the radiation sources of the radiation modules are arranged to emit radiation of different energies. For example, the first radiation source may be arranged to emit radiation of an energy above 100 kV and the second radiation source may be arranged to emit radiation of an energy below 100 kV. An increased contrast resolution is thereby obtained, and a contrast agent inserted into the patient can be seen more clearly providing an improved detection of e.g. atherosclerosis (hardening of the arteries) in the patient's blood vessels.

In still another embodiment of the invention, the first radiation module is arranged in a non-rotating fashion at a point along the axis of rotation. A flexible solution is thereby provided, wherein the imaging arrangement can be adapted to the particular use. Further, the cost of the imaging arrangement is also reduced.

The invention also relates to a method for obtaining imaging data of an object, whereby advantages similar to the above are achieved.

Further characteristics and features of the invention and advantages thereof will be evident from the detailed description of embodiments of the present invention given hereinafter and the accompanying figures, which are only given by way of illustration and are thus not limitative of the invention.

DETAILED DESCRIPTION OF EMBODIMENTS OF THE INVENTION

Figure 1:
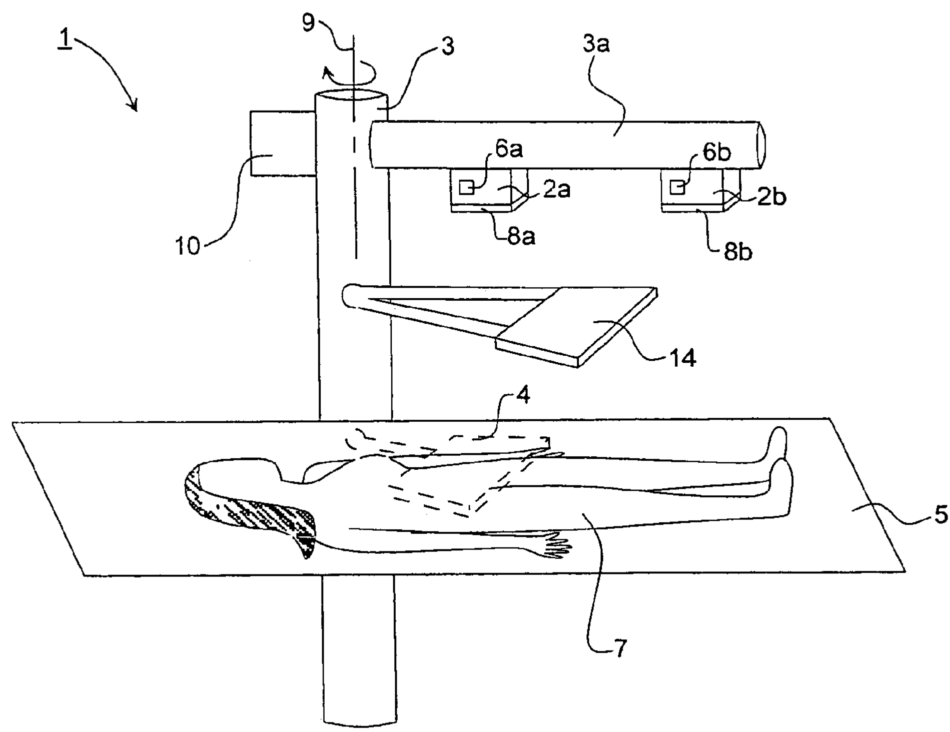
FIG. 1 illustrates schematically an imaging arrangement in accordance with the present invention.

FIG. 1 illustrates schematically the basic components of the present invention. An imaging arrangement 1 in accordance with the invention comprises one or more pairs of radiation modules 2*a*, 2*b* arranged on a support arm 3*a* of a support structure 3. The imaging arrangement 1 further comprises a radiation detector 4 arranged on the support structure 3 beneath a patient positioning table, in the following denoted object table 5. The radiation detector 4 and the radiation modules 2*a*, 2*b* are arranged on opposite sides of the patient positioning table 5 so as to enable the radiation detector 4 to detect radiation emitted from the radiation modules 2*a*, 2*b* and passed through a patient 7 or other object that is being imaged. The radiation modules 2*a*, 2*b*, the collimator 14 and the radiation detector 4 are rigidly connected to each other by means of the support structure 3, 3*a*.

The radiation modules 2*a*, 2*b* comprise a radiation source, preferably X-ray tubes and in the following denoted X-ray source 6*a*, 6*b*. Each X-ray source 6*a*, 6*b* preferably comprises a cathode, which emits electrons and an anode, which emits X-rays in response to being struck by the electrons. The X-ray source 6*a*, 6*b* is provided for emitting radiation of a suitable energy. The X-ray sources 6*a*, 6*b* of the two radiation modules 2*a*, 2*b* may be arranged to emit radiation of different energies, as described more in detail later on.

The radiation module 2*a*, 2*b* further comprises a filter arrangement 8*a*, 8*b*. The filter arrangement 8*a*, 8*b* is placed just beneath the X-ray source 6*a*, 6*b* and typically includes thin metallic foils acting as filters for absorbing the lowest (or highest) energy photons, which do not contribute significantly to the image quality. The filter arrangements 8*a*, 8*b* of the two radiation modules 2*a*, 2*b* may have different filter sections in front of the different X-ray sources 6*a*, 6*b* so that different radiation from the different X-ray sources 6*a*, 6*b* may be filtered differently.

The imaging arrangement 1 further comprises a collimator 14, which is also arranged on the support device 3. There can be one collimator in common for both radiation modules 2*a*, 2*b* or one separate collimator 14*a*, 14*b* (not shown) for each radiation module 2*a*, 2*b*. The collimator 14 may be a thin foil of e.g. tungsten with narrow radiation transparent slits. The slits are aligned with corresponding line-shaped sensitive areas or entrance slits of the radiation detector 4 so that X-ray bundles passing through the slits of the collimator 14 will reach the sensitive areas of the radiation detector 4.

The radiation detector 4 comprises a plurality of direction sensitive line detectors as is illustrated and described more in detail later on with reference to FIG. 2.

The support structure 3 may be any suitable support device to which the radiation modules 2*a*, 2*b*, the collimator 14 and the radiation detector 4 can be attached. The support structure 3 has an axis 9 of rotation as indicated in the figure. The object table 5 is preferably not supported by the support structure 3, but by another support structure (not illustrated).

A device, schematically illustrated and indicated at 10, is provided for rotating the support structure 3 around the axis 9 of rotation relative to the object table 5. The radiation modules 2*a*, 2*b*, the collimator 14 and the radiation detector 4 are arranged above one another and rotate together around the axis 9 of rotation relative to the object table 5; that is, are moved in a common rotational movement relative to the object to be examined. The object table 5 is arranged in the radiation path between the divergent radiation modules 2*a*, 2*b* and the radiation detector 4 during a short duration of a revolution of the support structure 3. During the rotation each of the line detectors of the radiation detector 4 is adapted to record a plurality of line images of radiation as transmitted through the object in a respective one of different angles.

The radiation module 2*a*, 2*b* is preferably active only when needed. That is, the X-ray radiation source 6*a*, 6*b* of the radiation module 2*a*, 2*b* only has to be switched on during the time it is scanned across the object table 5 and thus has to produce radiation for the measurement.

The imaging arrangement 1 further comprises a microprocessor or computer provided with suitable software for controlling the arrangement and readout and post-processing of the data recorded by the line detectors 16. Further, a power supply is included for supplying the detector and the microprocessor or computer with power and for driving a step motor or similar for driving the imaging arrangement 1 and the device 10 for rotating it. Further, image processing means is provided for calculating a three dimensional reconstruction of the object 7 based on tomosynthesis data provided from the line detectors.

It is noted that by means of the imaging arrangement 1, two images of the object 7 is taken simultaneously. That is, the radiation detector 4 is arranged to simultaneously record radiation emitted from the pair of radiation modules 2*a*, 2*b*.

Figure 2:
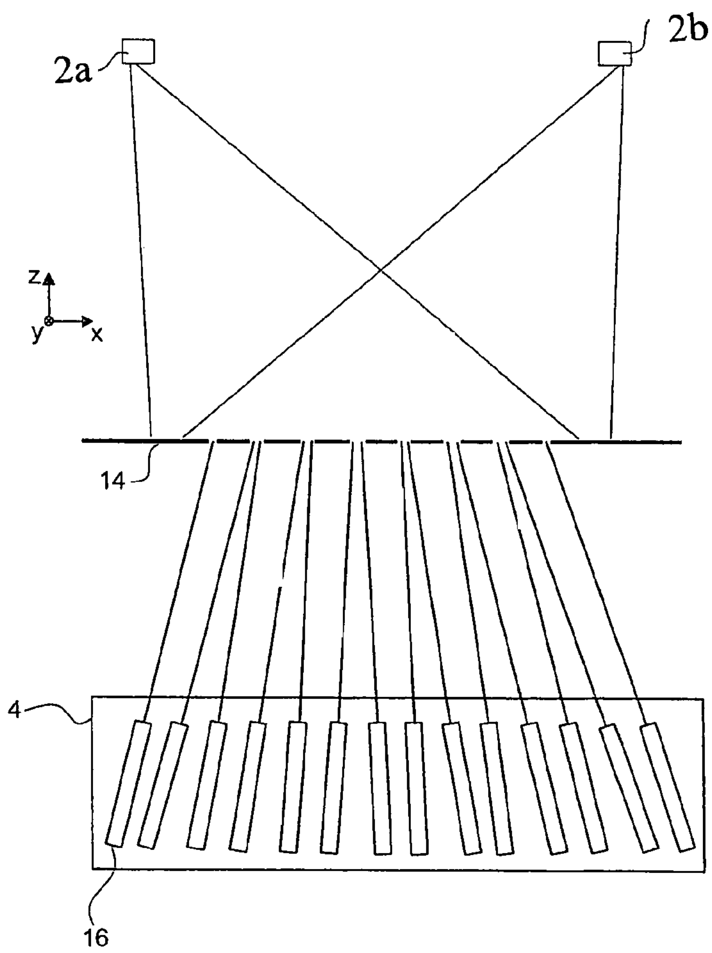
FIG. 2 illustrates the radiation detector of the imaging arrangement of FIG. 1.

FIG. 2 illustrates the radiation detector 4, which comprises a number of direction sensitive line detectors 16. Each line detector 16 extends in the y-direction in order to record one-dimensional images in the y-direction. Each of the line detectors 16 is preferably a gaseous-based ionization detector, wherein electrons freed as a result of ionization by ionizing radiation entered into the line detector are accelerated, and optionally avalanche amplified, in a direction essentially perpendicular to the direction of the entered ionizing radiation. Such line detector is referred to as a gaseous-based edge-on detector.

Such line detectors and arrays thereof are further described in the following US Patents issued to Tom Francke et al.: U.S. Pat. Nos. 6,337,482; 6,477,223; 6,476,397; 7,016,458; 7,006,597; 6,940,942; 6,970,533; 6,856,669; 6,873,682; 6,784,436; 6,794,656; 6,818,901; 6,627,897; 6,627,897; and 6,522,722, as well as in references therein, all of which being hereby incorporated by reference.

Each of the line detectors 16 may alternatively be any of a scintillator-based detector, a PIN-diode array, a TFT array, a CCD array, a gaseous-based detector, a liquid-based detector, a solid-state detector or a CMOS detector.

According to the invention, the line detectors 16 in the array are alternatively pointing towards different ones of the two radiation modules 2*a* and 2*b*. For example, every second line detector is pointing towards the X-ray source 6*a* and every second line detector is pointing towards the X-ray source 6*b*. Alternatively, small groups of line detectors may be pointing towards the respective X-ray sources 6*a*, 6*b*, e.g. groups of 2, 3 or 4 line detectors are pointing towards X-ray sources 6*a*, 6*b*, respectively.

The direction sensitivity of the line detectors 16 implies that each of them measures only radiation from the radiation source 6*a*, 6*b*, to which it is directed. Typically the opening angle of each line detector 16 in the x direction may be as low as 0.1 degrees.

If the line detectors 16 are gaseous-based edge-on detectors, each of them comprises readout strips that are essentially pointing towards either one of the radiation sources 6*a*, 6*b*. This means that the readout strips in each line detector 16 are arranged in a fan-like structure, wherein the extension lines of the readout strips converge in either one of the radiation sources 6*a*, 6*b*.

Figure 3:
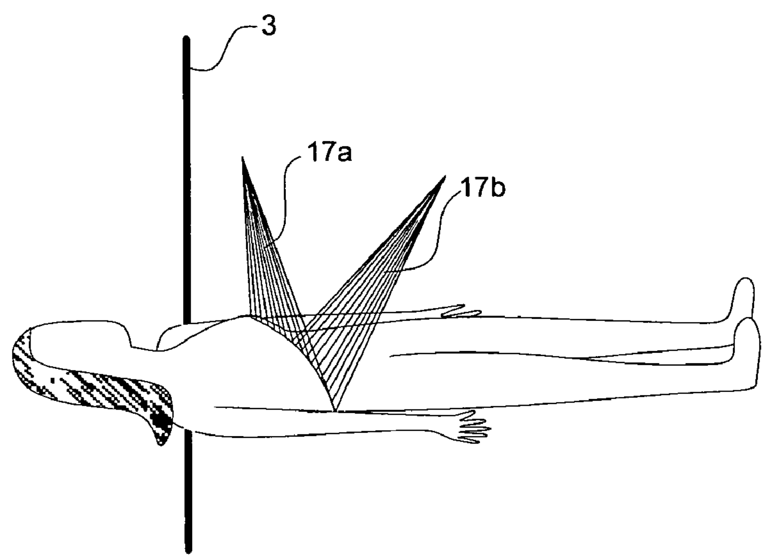
FIG. 3 illustrates schematically the imaging procedure in accordance with the present invention.

FIG. 3 illustrates schematically the imaging procedure utilizing the imaging arrangement 1 described above. In particular, the radiation emitted from the radiation modules 2*a*, 2*b* are shown schematically at 17*a* and 17*b*. For clarity, the sheet of radiation is shown only for one pair of line detectors, each pointing towards one of the radiation modules. Imaging data is obtained at high repetition rates for X-ray examination of the patient. During the rotation of the support structure 3 and thus rotation of the pair of radiation modules 2*a*, 2*b*, each of the line detectors 16 of the radiation detector 4 is adapted to record a plurality of line images of radiation as transmitted through the patient in a respective one of different angles.

Figure 4:
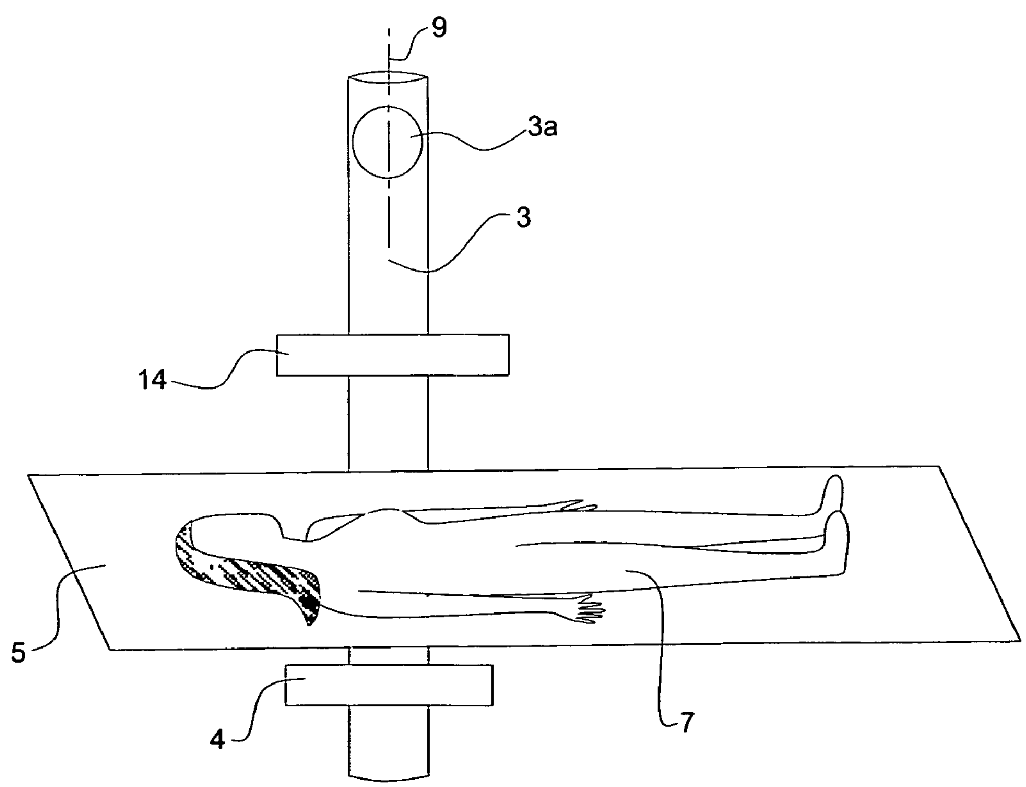
FIG. 4 illustrates, in a front view, an embodiment of the imaging arrangement in accordance with the present invention.

FIG. 4 illustrates an embodiment of the invention. The imaging arrangement 1 comprises the above-described support structure 3, including the radiation modules 2*a*, 2*b*, collimator 14 and radiation detector 4. The innermost radiation module 2*a* is preferably arranged close to the axis of rotation 9. The outermost radiation module 2*b* is arranged along the support arm 3*a* of the support structure 3, for example at a distance of 1-2 m from the axis of rotation 9.

The time resolution of the images is improved the more data that is gathered; the more consecutive heart beats during which measurements are made, the higher resolution is obtained. If the radiation detector 4 has a size that covers 20% of the circumference along which it travels, and if data is gathered at the rotational speed of 1 revolution per heart beat, then a time resolution of 20%*1 s=0.2 seconds is obtained. That is, the time during which measurements are made is then 0.2 s.

If data is gathered during the same phase of two consecutive heart beats (for example, during two revolutions of the imaging arrangement), then data from the first half of the radiation detector is used for the first heart beat ($1^{st}$ revolution), and data from the second half of the radiation detector is used for the second heart beat ($2^{nd}$ revolution). This gives a time resolution of about 0.1 s under the assumption that the heart beats are identical and that the imaging arrangement is rotated one revolution per heart beat.

There are studies indicating that the heart beats of a patient are sufficiently similar during five consecutive beats, and if beta-blockers are used the number is increased to ten. Assuming 5 and 10 heart beats, respectively, the time resolution would, in analogy with the above, be about 0.02 s and 0.01 s, respectively.

The rotational speed of the imaging arrangement 1 is synchronized with an electrocardiogram (ECG) examination of the patient. The radiation detector 4 can thereby be arranged so as to be in the particular phase of the heart beat of interest, during which data is to be gathered. If data is to be gathered during several heart beats, then the rotational speed is adjusted in accordance with the number of heart beats.

For example, if the measurements are to be performed for two consecutive heart beats with a rotational speed of about one revolution per heart beat, then the first (outermost) line detector in the radiation detector 4 is aligned so as to be under a particular part of the heart. If the radiation detector 4 has 80 line detectors, then the first 40 is used during the first revolution and thus first heart beat and data is gathered. During the next revolution (the next heart beat) the $41^{st}$ line detector should be aligned at the same part and data is again gathered. This thus implies that the rotational speed of the imaging arrangement 1 should be slightly higher that the heart rate of the patient.

The two radiation sources 6*a*, 6*b* can be arranged to emit radiation of different energies. One of the radiation sources 6*a* can have a hard X-ray spectrum (e.g. >100 kV) and the other radiation source 6*b* can have a soft X-ray spectrum (e.g. <100 kV). A hard spectrum is typically obtained by providing a high acceleration voltage on the radiation source and possibly filtering low-energetic X-rays by means of a filter. Conversely, a soft spectrum is typically obtained by means of low acceleration voltages, for example 60-80 kV or even lower and possibly by filtering high-energetic X-rays by means of a filter. It is to be noted that the radiation sources 6*a*, 6*b* may be arranged to emit radiation of equal energy.

An iodinated contrast agent absorbs low-energetic radiation to a greater extent than do tissue and blood, while high-energetic radiation is absorbed to a substantially equal extent of the contrast agent, tissue and blood. By subtracting the two images from one another, the iodide will become visible. By adding the images a regular X-ray image of the heart is obtained.

An increased resolution is obtained by such dual energy imaging, and a contrast agent inserted into the patient can be seen more clearly. An improved detection of e.g. atherosclerosis in the patient's blood vessels (that is, hardening of the arteries) is thereby provided.

Figure 5:
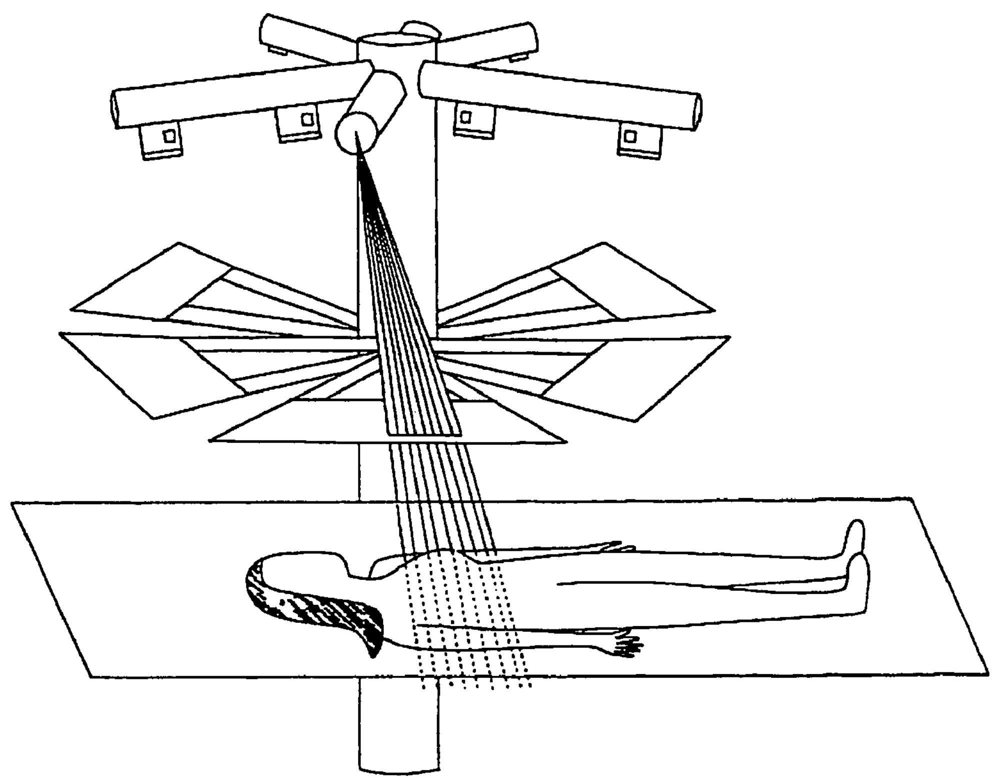
FIG. 5 illustrates another embodiment of the imaging arrangement in accordance with the present invention.

FIG. 5 illustrates another embodiment of the invention. In this embodiment, the support structure 3 comprises several pairs of radiation modules 2*a*, 2*b* and one radiation detector 4 associated with each pair of radiation modules 2*a*, 2*b*. Each arrangement of one pair of radiation modules 2*a*, 2*b* and their associated radiation detector 4 and collimator 14 is in the following denoted imaging device. When the support structure 3 rotates around the axis 9 of rotation relative to the object table 5, the object table 5 will successively be arranged in the radiation path between the radiation modules and radiation detectors of the imaging devices. During the rotation each of the imaging devices is adapted to record a plurality of line images of radiation as transmitted through the object in a respective one of different angles.

An advantage of this embodiment is that it is possible to take images of the heart in several of its phases simultaneously, or to use a lower rotational speed of the imaging arrangement 1 for providing images of the same heart phase.

Note that the radiation sources 6*a*, 6*b* of the imaging devices are preferably active in consecutive order. The two X-ray sources 6*a*, 6*b* of a particular imaging device thus only need to be switched on during the time it is scanned across the object table 5 that is, when they have to produce radiation for the measurement.

In yet another embodiment of the invention (not illustrated) one of the two radiation modules 2*a*, 2*b* is fixedly arranged close to the axis of rotation 9. The embodiment of FIG. 4 or 5 is thus modified in that the inner one of the radiation modules 2*a*, 2*b* does not rotate. This fixedly arranged radiation module 2*a* is consecutively paired with each of the radiation modules 2*b* arranged at the outer part of the support arm 3*a* on which the radiation modules 2*b* are arranged. That is, the fixedly arranged radiation module 2*a* is used as the second X-ray source 6*a* for each of the one or more imaging devices. The fixedly arranged radiation module 2*a* is arranged to emit radiation simultaneously with each of the outer radiation sources 2*b*.

Today, the catheter used to administer the contrast agent at the area to be imaged, for example the heart, is usually threaded into an artery in the groin of the patient and the tip is advanced through the arterial system into the area being imaged, e.g. the heart. In order to provide a sufficient contrast resolution, large amounts of contrast agent containing iodide is inserted. The contrast agent also has a high concentration of iodide.

The present invention provides an improved contrast resolution, that is, the ability of the fluoroscopy to distinguish between various contrasts of the acquired image. By means of the increased contrast resolution the threading of the catheter into the groin can be avoided. Instead, the contrast agent may be injected in the forearm. This is a known procedure; the concentration of the contrast agent in the heart is decreased, but this also means that it is more difficult to obtain images of high quality. By means of the increased contrast resolution the amount of iodinated contrast agent required can be minimized and the health hazards related to such procedures can be reduced.

The imaging arrangement in accordance with the invention provides high-quality images, and enables the medical examiner to see how the contrast agent disperses in the blood and onwards to the heart. It is, for example, possible to see whether some parts of the heart obtains less or none contrast agent, which would indicate a impaired flow of blood in the cardiovascular system. All this can, in accordance with the invention, be imaged three-dimensionally with high resolution.

The three-dimensional images have high spatial resolution in all three dimensions, since the radiation detector used have small pixel sizes. As a comparison, prior art imaging systems such as fluoroscopy, have pixel sizes in the range of 200-600 μm, which can be compared with the present imaging arrangement having pixel sizes of about 100 μm. Further, the high resolution provided is also owing to the fact that the images of the patient is taken in many angles.

Further, the present invention provides high time resolution in which the resolution is not affected by the heart's motion. This is achieved by the innovative imaging arrangement, in which the radiation detector passes under the heart during a short duration of the heart beat cycle.

Owing to the low radiation dose required, the arrangement of the present invention can be used as part of routine physical examinations. That is, three-dimensional images of for example the heart can be taken in preventive purpose, that is, tests performed on patients without any clinical indication of disease (so-called screening). High-quality images of internal organs can be obtained without posing the patient to health risks.

Figure 6:
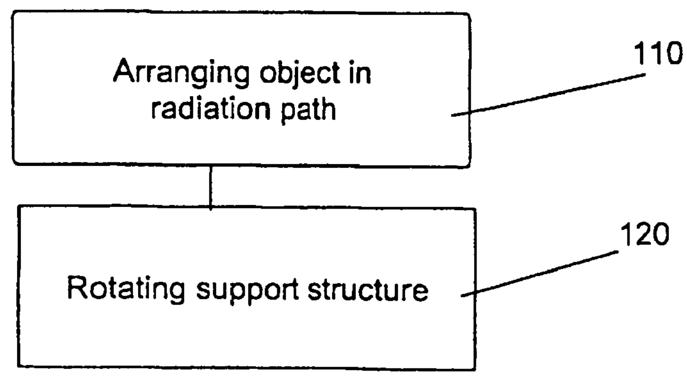
FIG. 6 illustrates a flow chart of steps included in a method in accordance with the present invention.

The invention is also related to a method for obtaining imaging data of an object using the imaging arrangement 1 as described above. With reference to FIG. 6, the method comprises the steps of: arranging, in step 110, the object 7 in the radiation path between the radiation sources 6*a*, 6*b* and the radiation detector 4, and rotating, in step 120, the support structure 3 around its axis of rotation 9 relative the object 7. In angiography, that is when the object 7 is for example the heart of a patient, the step of rotating the support structure 3 may comprise the further step of adapting the rotational speed in dependence on the heart rate and/or the number of heart beats being imaged in a manner previously described.

In summary, by providing two X-ray sources arranged in accordance with the inventive arrangement, an improved resolution is obtained, and in particular in the vertical direction. Further, dual energy imaging is also enabled, for example a dual energy angiography.

In the preceding detailed description, the invention is described with reference to specific exemplary embodiments thereof. Various modifications and changes may be made thereto without departing from the scope of the invention as set forth in the claims. The specification and drawings are, accordingly, to be regarded in an illustrative rather than a restrictive sense.

The invention claimed is:

1. An imaging arrangement for obtaining imaging data of an object, comprising:

a support structure having an axis of rotation and comprising means for rotating said support structure;

a pair of first and second radiation modules fixedly arranged on said support structure along a radius perpendicular to said axis of rotation, said radiation modules being arranged in parallel to each other along said radius, wherein each of said radiation modules comprises a radiation source simultaneously emitting X-ray radiation, a radiation detector for detecting X-ray radiation as emitted from said radiation modules and passed through the object being imaged, wherein said radiation detector comprises a number of direction sensitive line detectors, each being directed towards either one of said two radiation sources to allow a ray bundle of X-ray radiation to enter the line detector, and a collimator arranged between, as seen in a direction parallel to said axis of rotation, said radiation modules and said radiation detector.

2. The imaging arrangement as claimed in claim 1, wherein each of said number of direction sensitive line detectors is adapted to record a plurality of line images of X-ray radiation as transmitted through said object from said pair of radiation modules.

3. The imaging arrangement as claimed in claim 1, wherein every second line detector is arranged to record X-ray radiation from said first radiation module and every remaining line detector is arranged to record X-ray radiation from said second radiation module.

4. The imaging arrangement as claimed in claim 1, comprising two or more pairs of first and second radiation modules, wherein each pair has an associated collimator and radiation detector, and wherein the radiation detector of each pair is arranged to consecutively image said object during a revolution of said imaging arrangement.

5. The imaging arrangement as claimed in claim 1, further comprising an object table on which said object is arranged, and wherein said object table is arranged in the X-ray radiation path between the radiation modules and the radiation detector.

6. The imaging arrangement as claimed in claim 1, wherein each of said radiation modules further comprises a respective filter arrangement arranged in front of each respective radiation source.

7. The imaging arrangement as claimed in claim 1, wherein said radiation sources of said radiation modules are arranged to emit X-ray radiation of different energies.

8. The imaging arrangement as claimed in claim 7, wherein the radiation source of the first radiation module is arranged to emit X-ray radiation of an energy above 100 kV and the radiation source of said second radiation module is arranged to emit X-ray radiation of an energy below 100 kV.

9. The imaging arrangement as claimed in claim 1, wherein said radiation modules are arranged at a distance of 1 meter from each other.

10. The imaging arrangement as claimed in claim 1, wherein said radiation detector is arranged to simultaneously record X-ray radiation emitted from said pair of radiation modules.

11. The imaging arrangement as claimed in claim 1, wherein said imaging data is tomosynthesis data and said imaging arrangement further comprises an image processor for calculating a three dimensional reconstruction of said object based on said tomosynthesis data.

12. The imaging arrangement as claimed in claim 1, wherein the first radiation module is arranged in a non-rotating fashion at a point along said axis of rotation.

13. A method for obtaining imaging data of an object using an imaging arrangement comprising a support structure having an axis of rotation and comprising a device for rotating said support structure; a pair of first and second radiation modules fixedly arranged on said support structure along a radius perpendicular to said axis of rotation, said radiation modules being arranged in parallel to each other along said radius, wherein each of said radiation modules comprises a radiation source simultaneously emitting X-ray radiation; a radiation detector for detecting X-ray radiation as emitted from said radiation modules and passed through the object being imaged, wherein said radiation detector comprises a number of direction sensitive line detectors, each being directed towards either one of said two radiation sources to allow a ray bundle of X-ray radiation to enter the line detector, and a collimator arranged between, as seen in a direction parallel to said axis of rotation, said radiation modules and said radiation detector, said method comprising the steps of:

arranging said object in the X-ray radiation path between the radiation sources and the radiation detector, and rotating said support structure around said axis of rotation relative to said object.

14. The method as claimed in claim 13, wherein said object is the heart of a patient and said rotating said support structure comprises adapting the rotational speed in dependence on the heart rate and/or the number of heart beats being imaged.

* * * * *